(12) United States Patent
Zhang et al.

(10) Patent No.: US 11,337,926 B2
(45) Date of Patent: May 24, 2022

(54) COLON-TARGETED COMPOSITION OF BIOLOGICAL ACTIVE COMPONENT AND APPLICATION THEREOF

(71) Applicant: NANJING HEALSOUL LIFE SCIENCE AND TECHNOLOGY CO., LTD., Nanjing (CN)

(72) Inventors: Junshou Zhang, Nanjing (CN); Chaonan Sun, Nanjing (CN); Hao Zhang, Nanjing (CN)

(73) Assignee: NANJING HEALSOUL LIFE SCIENCE AND TECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 16/349,093

(22) PCT Filed: Nov. 9, 2017

(86) PCT No.: PCT/CN2017/110074
§ 371 (c)(1),
(2) Date: May 10, 2019

(87) PCT Pub. No.: WO2018/086550
PCT Pub. Date: May 17, 2018

(65) Prior Publication Data
US 2019/0274960 A1    Sep. 12, 2019

(30) Foreign Application Priority Data

Nov. 11, 2016 (CN) .......................... 201611013848.3

(51) Int. Cl.
| | |
|---|---|
| A61K 9/20 | (2006.01) |
| A23L 33/135 | (2016.01) |
| A61K 35/744 | (2015.01) |
| A61K 35/745 | (2015.01) |
| A61K 35/747 | (2015.01) |
| A61K 47/38 | (2006.01) |
| A61P 1/00 | (2006.01) |
| A61K 9/00 | (2006.01) |
| A61K 35/00 | (2006.01) |

(52) U.S. Cl.
CPC .......... *A61K 9/2054* (2013.01); *A23L 33/135* (2016.08); *A61K 9/20* (2013.01); *A61K 9/2095* (2013.01); *A61K 35/744* (2013.01); *A61K 35/745* (2013.01); *A61K 35/747* (2013.01); *A61K 47/38* (2013.01); *A61P 1/00* (2018.01); *A23V 2002/00* (2013.01); *A61K 9/0056* (2013.01); *A61K 2035/115* (2013.01)

(58) Field of Classification Search
None
See application file for complete search history.

(56) References Cited

U.S. PATENT DOCUMENTS

2007/0098784 A1* 5/2007 Moger ................. A61K 9/2031
424/451

FOREIGN PATENT DOCUMENTS

| CN | 1853655 A | 11/2006 | |
|---|---|---|---|
| CN | 1921838 A | 2/2007 | |
| CN | 102106925 A | 6/2011 | |
| CN | 105120847 A | 12/2015 | |
| WO | 9824412 A2 | 6/1998 | |
| WO | WO-2005079753 A2 * | 9/2005 | ........... A61K 9/2018 |
| WO | 2015087259 A1 | 6/2015 | |
| WO | WO-2016003870 A1 * | 1/2016 | ........... A61K 35/744 |

OTHER PUBLICATIONS

Rahman et al. ("Evaluation of Various Grades of Hydroxypropylmethylcellulose Matrix Systems as Oral Sustained Release Drug Delivery systems", Journal of Pharmaceutical Sciences and Research, vol. 3(1), (2011), p. 930-938) (Year: 2011).*
Khan ("Swelling and Release Studies of Stavudine Hydrophilic Matrices containing Different Grades of Hydroxypropyl Methylcellulose", World Journal of Pharmaceutical Research, vol. 2(6), (2013), p. 2696-2705) (Year: 2013).*
Internet article DAPI, obtained from the Wikipedia website: https://en.wikipedia.org/wiki/DAPI (date unknown).*
International Search Report for International Application No. PCT/CN2017/110074, dated Feb. 11, 2018, 2 pages.
English translation of Official Action for RU Application No. 2019116519/04(031501), dated Feb. 19, 2020, 9 pages.
EPO Extended European Search Report for Application No. 17869993.0 dated May 8, 2020; 9 pp.
Marvole, Tuuli et al., "Neutron activation based gamma scintigraphic evaluation of enteric-coated capsules for local treatment in colon," International Journal of Pharmaceutics 349 (2008), pp. 24-29.
English Translation of JPO Office Action for Patent Application JP 2019-546961 dated Jun. 1, 2021; 6 pp.
Saravanan, Muniyandy et al., "Hydroxypropyl Methylcellulose Based Cephalexin Extended Release Tablets: Influence of Tablet Formulation, Hardness and Storage on in Vitro Release Kinetics," Chem. Pharm. Bull. 51, vol. 8, pp. 978-983 (2003).
Vemula, Sateesh Kumar et al., "Colon Specific Controlled Release Matrix Tablets of Flurbiprofen: Development and Characterization," Asian Journal of Pharmaceutical and Clinical Research, vol. 5, Suppl. 4, pp. 92-96 (2012).
Ramanathan et al. Formulation of floating tablets of mefenamic acid with different grades of Hydroxy propyl methyl cellulose polymer and studying the release profiles. International Journal of Drug Development & Research, 2010, vol. 2, issue 3, pp. 599-604.

* cited by examiner

*Primary Examiner* — Sin J Lee
(74) *Attorney, Agent, or Firm* — Armstrong Teasdale LLP

(57) ABSTRACT

A colon-targeted composition of a biological active component is disclosed, as well as formulations and preparation methods thereof. The colon-targeted composition of a biological active component includes in weight percentage: 10-99% hydroxypropyl methylcellulose, 1-60% biological active component and 0-80% auxiliary material, wherein the viscosity of hydroxypropyl methylcellulose is greater than 1,000 mPa·s. The colon-targeted composition of a biological active component has an improved colon-targeted effect and improves the bioavailability and in vivo activity of the biological active component.

7 Claims, 1 Drawing Sheet

COLON-TARGETED COMPOSITION OF BIOLOGICAL ACTIVE COMPONENT AND APPLICATION THEREOF

CROSS-REFERENCE TO RELATED APPLICATIONS

This application is a U.S. National Phase Application of PCT/CN2017/110074, filed Nov. 9, 2017, which claims the benefit of priority to CN Application No. 201611013848.3, filed Nov. 11, 2016, the contents of which are hereby expressly incorporated by reference in their entirety.

FIELD OF THE INVENTION

The present application belongs to the fields of food, health product and medicine, and specially relates to a colon-targeted composition of a biological active component as well as formulations and preparation methods thereof.

BACKGROUND OF THE INVENTION

Biological active component is a large class of components with physiological activity. Taking appropriate biological active component may play an important role in the nutrition improvement, the prevention and treatment of diseases and health care. However, for most biological active components, when they are given orally, the following problems often exist: 1) the activities of most biological active components will be destroyed considerably by the environment of upper digestive tract (e.g. gastric acid, digestive enzyme and the like), so that these biological active components could not act fully; 2) after given orally, the biological active component largely exists in the stomach and small intestine, where the component could not be absorbed and utilized advantageously by human body, resulting in corresponding damage(s) to the body easily; 3) harsh conditions for production and processing (e.g. the temperature, the humidity, and the incorporation of some solvents) will destroy the activity of the component.

Directing to the above problems, a colon-targeted delivery system is capable of avoiding the release of active substance in stomach, duodenum, jejunum and ileum, but delivering the active substance to the colon of the patient directly and releasing in the colon, by using an appropriate method. In this way, the local concentration of the active substance in colon will be increased, so that the active substance could be absorbed and play its role in treatment and healthcare fully. Meanwhile, the release of active substance in stomach and small intestine is avoided, so that adverse reactions will be reduced and bioavailability of the active substance, which is easily destroyed by gastric acid or metabolized by pepsin or pancreatic enzymes, will be improved. Accordingly, the above-mentioned deficiencies are remedied largely.

The dosage forms are designed in combination with modern pharmaceutical preparation technologies. Delivery systems for colon-targeted administration are mainly divided into the following classes: time-delayed drug delivery system, drug delivery system depending on pH, enzyme-triggered drug delivery system, drug delivery system depending on the pressure, and prodrug-based drug delivery system. The time-delayed to drug delivery system avoids the drug releasing in stomach and small intestine but enable the drug to be released upon reaching the colon, by using its time-delayed characteristics, that is from 5 to 6 hours is needed for the substance to pass through the stomach and small intestine in sequence and then reach the colon. The drug delivery system depending on pH utilizes the different pH in gastrointestinal tract to achieve the purpose of release in colon by selecting the coating method. The coating-preparation process is complex. Also, this process needs to use a solvent which is required to be volatilized fully under certain temperature. Thus, such process is very likely to decrease the activity of the biological active component significantly. Although people currently pay great attention to the enzyme-triggered drug delivery system, the drug delivery system depending on the pressure and the prodrug-based drug delivery system, they are limited by unconventionality, inherent complexity, and even the requirement for specialized devices and complex processing steps. Such limitation not only increases the complexity of the research and development but also decreases largely the possibility of producing the product in large scale.

The activity of a biological active component, in particular the beneficial microorganism, is difficult to resist the influence of slightly higher temperature or humility, solvent or other materials during the preparation process of the relevant preparations. Thus, the research and development of its colon-targeted delivery system is largely limited. The more complex preparation process often leads to more destruction to the activity. As a result, there is no colon-targeted probiotics relevant product available in the market until now.

The existing probiotic preparation technologies enable probiotic bacteria to pass through the stomach and be released in small intestine. However, even so, if the probiotics gather excessively in the small intestine, safety problems such as serious intestinal dysbacteriosis may appear (CN200910229403.2). Although the existing probiotic preparation technologies can deliver the probiotics to the distal sections of the gastrointestinal tract, including the ileum, they could not achieve the targeted delivery to the colon directly, so that the utilization rate of the probiotics cannot reach the best (US2016022592). The existing probiotic preparation technologies also have a safety to problem from the auxiliary materials used (ALBERTINI B, VITALI B, PASSERINI N, et al. Development of microparticulate systems for intestinal delivery of *Lactobacillus acidophilus* and *Bifidobacterium lactis* [J]. European Journal of Pharmaceutical Sciences, 2010, 40 (4):359-366.) The existing probiotic preparation technologies cannot avoid the influences of the solvent used in the preparation process, the increased temperature or humidity during the preparation and the like on the activity of probiotics (KLEMMER K J, KORBER D R, NICHOLAS H, et al. Pea proteinbased capsules for probiotic and prebiotic delivery [J]. International Journal of Food Science and Technology, 2011, 46 (11):2248-2256.) In the existing probiotic preparation technologies, to meet the requirement of effective oral dosage forms, the required auxiliary materials are large in volume and thus the carried viable count is relatively low. Furthermore, the existing probiotic preparation technologies are complex in preparation process and are difficult to be used for industrial production (CALINESCU C, MATEESCU M A. Carboxymethyl high amylase starch: chitosan self-stabilized matrix for probiotic colon delivery [J]. European Journal of Pharmaceutics and Biopharmaceutics, 2008, 70 (2):582-589).

SUMMARY OF THE INVENTION

The objective of the present invention is to provide a colon-targeted composition of a biological active component as well as the formulation containing the composition, by which most of the biological active component can pass through the stomach and small intestine and be released after reaching colon, so that the bioavailability of the biological active component is improved, so as to play its activity in-vivo better. Accordingly, the above-mentioned problems existed in the prior art are solved.

The present invention is achieved by the following ways:

In one aspect, the present invention provides a hydroxypropyl methylcellulose (HPMC)-based colon-targeted composition of a biological active component, which comprises hydroxypropyl methylcellulose, biological active component and auxiliary material, wherein the weight percentage of the hydroxypropyl methylcellulose is 10-99%, to the weight percentage of the biological active component is 1-60%, and the weight percentage of the auxiliary material is 0-80%; further preferably, the weight percentage of the hydroxypropyl methylcellulose is 40-90%, the weight percentage of the biological active component is 10-40%, and the weight percentage of the auxiliary material is 0-50%; wherein, the viscosity of the hydroxypropyl methylcellulose is more than 1000 mPa·s.

Preferably, the viscosity of the hydroxypropyl methylcellulose is 15,000 mPa·s-200,000 mPa·s.

Preferably, the biological active component is microorganisms. More preferably, the microorganism is probiotics, and the probiotics comprise one or more of bifidobacteria, lactobacilli and gram-positive cocci which are allowed to be used in foods, health products and medicines; preferably, the bifidobacteria are one or more of *Bifidobacterium lactis, Bifidobacterium infantis, Bifidobacterium bifidum, Bifidobacterium longum, Bifidobacterium breve*, and *Bifidobacterium adolescentis*; the lactobacilli are one or more of *Lactobacillus acidophilus, Lactobacillus casei, Lactobacillus crispatus, Lactobacillus delbrueckii* subspecies *bulgaricus* (*Lactobacillus bulgaricus*), *Lactobacillus delbrueckii* subspecies, *Lactobacillus fermentum, Lactobacillus gasseri, Lactobacillus helveticus, Lactobacillus johnsonii, Lactobacillus paracasei, Lactobacillus planterum, Lactobacillus reuteri, Lactobacillus rhamnosus* and *Lactobacillus salivarius*; the gram-positive cocci are one or more of *Streptococcus faecalis* and *Lactococcus*.

Further preferably, the amount of probiotics in the colon-targeted composition is 0.001-120 billion cfu/g.

Preferably, the auxiliary material comprises a nutrient substance beneficial to the survival stability of the biological active component, wherein the nutrient substance may be prebiotics, such as fructo-oligosaccharide, galacto-oligosaccharide, xylo-oligosaccharide, lactosucrose, soybean oligosaccharide, pectin, inulin, cranberry powder, and the like, vitamins and/or sugar alcohols.

Preferably, the auxiliary material further comprises a medicinal auxiliary material or a food additive which is beneficial to colon-targeted delivery of the biological active component, such as pectin, sodium alginate and chitosan.

Preferably, the auxiliary material further comprises other auxiliary materials which can optimize the property of the formulation itself, such as additional binders (arabic gum, guar gum, alginic acid, hydroxymethyl cellulose, dextrin, carbomer, maltose, gelatin, glucose, ethyl cellulose, methyl cellulose, polyethylene oxide or povidone), fillers (starch, compressible starch, modified starch, sorbitol, mannitol, microcrystalline cellulose, powdered sugar, dextrin, inorganic salt, anhydrous lactose and calcium lactate), lubricants (magnesium stearate, stearic acid, mineral oil, polyethylene glycol, talcum powder and silicon dioxide), and disintegrating agents (sodium carboxymethyl starch, low-substituted hydroxypropyl cellulose, croscarmellose sodium, crospovidone and dry starch).

In a second aspect, the present invention provides a colon-targeted formulation of a biological active component, which comprises the colon-targeted composition of the biological active component of the present invention.

Preferably, the dosage form of the formulation is a tablet; more preferably, the tablet has a mass of ≤500 mg per tablet and a diameter of ≤10 mm. Such dosage form can further contribute to the release of the biological active component in colon where a large number of bacterial flora exists, while the biological active component in this dosage form is only released partially or in a small amount in the stomach, small intestine and ileum.

In a third aspect, the use of the colon-targeted composition of a biological active component of the present invention in the preparation of a colon-targeted formulation of a biological active component is provided.

In a fourth aspect, a preparation method for the colon-targeted formulation of a biological active component of the present invention, comprising:

(1) mixing hydroxypropyl methylcellulose, biological active component and auxiliary material under the operation temperature of <28° C. and the humidity of <40%; and (2) dry-pressing the mixture into tablets directly, or dry granulating followed by pressing into tablets, is provided.

In the present invention, hydroxypropyl methylcellulose is combined with biological active component for the first time. The present colon-targeted tablet of the biological active component is formulated through dry-pressing the powder directly or dry granulating followed by pressing into tablets, utilizing the sustained release character and adhesive effect of hydroxypropyl methylcellulose. In this way, the adverse effects of the solvent and temperature used in wet granulating and the common coating methods in existing articles related to colon-targeting on the activity of the biological active component are avoided. Further, the preparation process is simple and easy to industrialize. Due to the multiple effects of hydroxypropyl methylcellulose, the prepared colon-targeted tablet of the biological active component, compared with commercially available biological active component tablets, enables the biological active component to resist the environment in stomach and small intestine without being metabolized and decomposed, thereby passing through the stomach and small intestine and releasing after reaching the colon. As a result, the possible harm factors to the small intestine can be reduced and the bioavailability of the biological active component will be improved. Accordingly, its in-vivo activity will be better exerted. Particularly, for the probiotic formulation, the use of other auxiliary materials can be greatly reduced, so that the bacterium capacity of each tablet is remarkably improved. In consequence, the daily administration amount is reduced to 1-2 pieces from the common 9 pieces for the commercially available tablets. Further, the tablet can be smaller in size and more convenient to swallow.

Compared with the prior art, the present composition has a significantly improved colon targeting effect; and the present composition may adopt food-grade auxiliary materials, leading to extremely high safety. In addition, the present process is simple and can be applied in industrial production easily. Therefore, the present invention has great significance for the development in food, health products and drug industries.

DETAILED DESCRIPTION OF THE INVENTION

Figure 1:
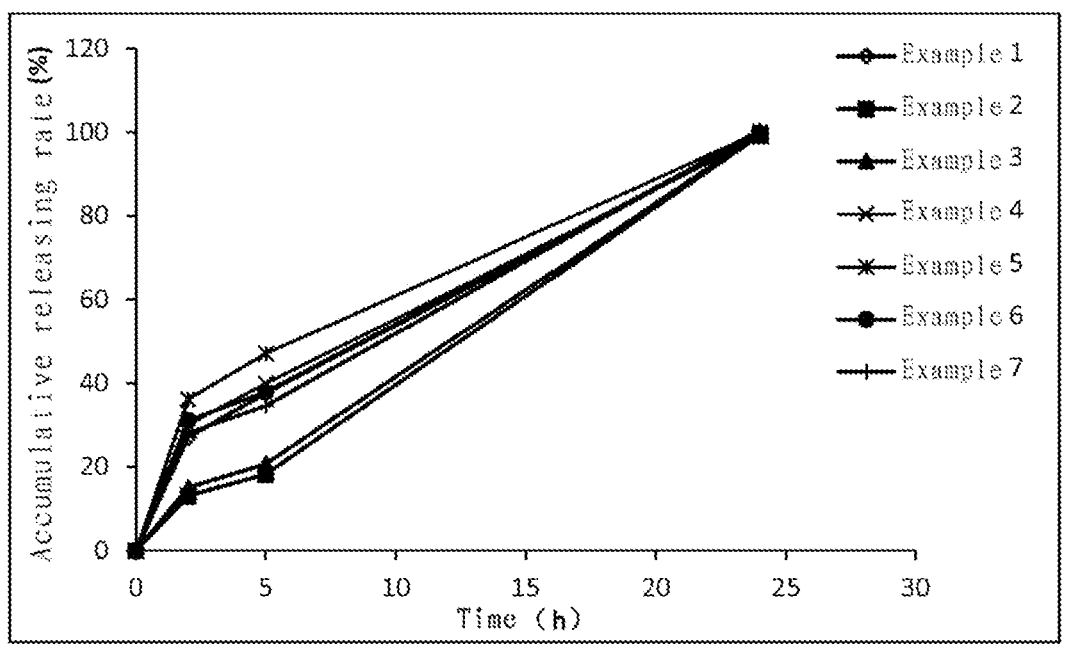
FIG. 1. Graph of dissolution curves of the tablets of Examples 1-7 upon subjecting to artificial gastric juice for 2 hours, artificial intestinal juice for 3 hours and artificial colon liquid for 18 hours in sequence.

The present technical solutions and the effects thereof are further described through the following specific examples. It should be understood that the examples of the present invention are only used to illustrate specific embodiments of the present invention, and is not used for limiting the protection scope of the present invention. The simple improvement to the present invention based on the present concept is within the claimed scope of the invention.

Unless otherwise specified, reagents or instruments used in the following examples are all conventional reagents or instruments, and are commercially available; the operation methods used are conventional methods in the field, and combined with their cognitive level and experimental ability, one skilled in the art can implement the experimental processes described herein to obtain corresponding results.

The probiotic bacteria powders used in the present invention comprise: *Bifidobacterium lactis* BLa80, *Bifidobacterium longum* BL21, *Lactobacillus acidophilus* LA85 and *Bifidobacterium bifidum* BBi32, from Jiangsu Zishiweikang Biotechnology co., Ltd; *Lactobacillus rhamnosus* R11, *Bifidobacterium longum* R175 and *Bifidobacterium lactis lafti* B84, from LALLEMAND company, France. The hydroxypropyl methylcellulose K4M, K15M and K100M used herein are from Anhui Sunhere Excipients co., Ltd. Hydroxypropyl methylcellulose K100LV and K200M used herein are from the Dow chemistry, US.

Example 1

Formula: 85 wt % of hydroxypropyl methylcellulose (HPMC K15M, with a viscosity of 15,000 mPa·s), and 15 wt % of *Bifidobacterium lactis* BLa80 powder (with a viable count of $1.0*10^{11}$ cfu/g).
Preparation Method:
(1) The materials were mixed uniformly according to the amounts shown in the formula, passed through a 100-mesh sieve, and uniformly mixed again;
(2) The powder mixture was subjected to granulating using GL2-25 type dry granulator (Zhangjiagang Create Mechanical Manufacturing co., LTD) and pressing into tablets. Each single tablet had a weight of 150 mg and a diameter of 8 mm. The viable count of *Bifidobacterium lactis* contained in the tablet was $1.5*10^{10}$ cfu/g.

Example 2

Formula: 65 wt % of hydroxypropyl methylcellulose (HPMC K200M, with a viscosity of 200,000 mPa·s), 30 wt % of *Lactobacillus rhamnosus* R11 powder (with a viable count of $1.5*10^{11}$ cfu/g), and 5 wt % of magnesium stearate.
Preparation Method:
(1) The materials were mixed uniformly according to the amounts shown in the formula;
(2) The mixture powder was subjected to dry pressing into tablets directly. Each single tablet had a weight of 450 mg and a diameter of 10 mm. in the tablet, the viable count of *Lactobacillus rhamnosus* was $4.5*10^{10}$ cfu/g.

Example 3

Formula: 65 wt % of hydroxypropyl methylcellulose (HPMC K100M, with a viscosity of 100,000 mPa·s), 30 wt % of *Lactobacillus acidophilus* LA85 powder (with a viable count of $1.0*10^{11}$ cfu/g), and 5 wt % of magnesium stearate.
Preparation Method:
(1) The materials were mixed uniformly according to the amounts shown in the formula;
(2) The mixture powder was subjected to dry pressing into tablets directly. Each single tablet had a weight of 300 mg and a diameter of 10 mm. In the tablet, the viable count of *Lactobacillus acidophilus* was $3.0*10^{10}$ cfu/g.

Example 4

Formula: 45 wt % of hydroxypropyl methylcellulose (HPMC K200M, with a viscosity of 200,000 mPa·s), 25 wt % of *Bifidobacterium lactis* BLa80 powder (with a viable count of $1.0*10^{11}$ cfu/g), 25 wt % of *Bifidobacterium longum* BL21 powder (with a viable count of $1.5*10^{11}$ cfu/g), and 5 wt % of magnesium stearate.
Preparation Method:
(1) The materials were mixed uniformly according to the amounts shown in the formula;
(2) The mixture powder was subjected to dry pressing into tablets directly. Each single tablet had a weight of 300 mg and a diameter of 10 mm. In the tablet, the viable count of *Bifidobacterium lactis* was $2.5*10^{10}$ cfu/g and the viable count of *Bifidobacterium longum* was $3.75*10^{10}$ cfu/g.

Example 5

Formula: 70 wt % of hydroxypropyl methylcellulose (HPMC K4M, with a viscosity of 4,000 mPa·s), 20 wt % of anhydrous lactose, 5 wt % of maltitol, 3 wt % of *Bifidobacterium bifidum* BBi32 powder (with a viable count of $1.5*10^{11}$ cfu/g), 1 wt % of silicon dioxide and 1 wt % of magnesium stearate.
Preparation Method
(1) The materials were mixed uniformly according to the amounts shown in the formula; and
(2) The mixture powder was subjected to dry pressing into tablets directly. Each single tablet had a weight of 300 mg and a diameter of 10 mm. In the tablet, the viable count of *Bifidobacterium bifidum* was $4.5*10^{9}$ cfu/g.

Example 6

Formula: 13 wt % of hydroxypropyl methylcellulose (HPMC K100M, with a viscosity of 100,000 mPa·s), 30 wt % of *Bifidobacterium longum* R175 powder (with a viable count of $5*10^{10}$ cfu/g), 25 wt % of isomaltitol, 15 wt % of inulin, 10 wt % of calcium lactate, 5 wt % of pectin and 2 wt % of magnesium stearate.
Preparation Method:
(1) The materials were mixed uniformly according to the amounts shown in the formula; and (2) The mixture powder was subjected to dry pressing into tablets directly. Each single tablet had a weight of 300 mg/tablet, and a diameter of 10 mm. In the tablet, the viable count of *Bifidobacterium longum* was $1.5*10^{10}$ cfu/g.

Example 7

Formula: 45 wt % of hydroxypropyl methylcellulose (HPMC K100M, with a viscosity of 100,000 mPa·s), 20 wt % of fructo-oligosaccharide, 15 wt % of *Lactobacillus acidophilus* R418 powder (with a viable count of $1.5*10^{11}$ cfu/g), 10 wt % of *Bifidobacterium lactis lafti* B84 powder (with a viable count of $1*10^{11}$ cfu/g.), 5 wt % of cranberry powder, and 5 to wt % sorbitol.
Preparation Method:
(1) The materials were mixed uniformly according to the amounts shown in the formula; and
(2) The mixture powder was subjected to granulating using dry type granulator followed by pressing into tablets. Each single tablet had a weight of 450 mg and a diameter of 10 mm. In the tablet, the viable count of *Lactobacillus acidophilus* was $2.25*10^{10}$ cfu/g and the viable count of *Bifidobacterium lactis* was $1.0*10^{10}$ cfu/g.

Experimental Example 1: Dissolution Tests for the Examples of the Present Invention Since the probiotics were sensitive to both temperature and water and it was needed to take dissolution liquids at different time points for dissolution tests, a model drug for evaluating the drug release property in colon, 5-aminosalicylic acid, instead of the probiotics, was used in the tests.

According to the Chinese pharmacopoeia (2015 edition, part four, 0931 dissolution rate and releasing rate determination methods, the first method-rotary basket method, 50 r/min, 37° C.), the tablet prepared using the method and formula in the above-mentioned examples (in which the probiotics are replaced by 5-aminosalicylic acid in corresponding amount) was placed into a rotary basket, and subjected to artificial gastric juice (pH1.2) for 2 h, artificial intestinal juice (pH6.8) for 3 hours and artificial colon fluid (pH7.8) for 18 hours in sequence before a dissolution test. The dissolution results of the tablets from the examples are shown in FIG. 1. The release percentages in colon are shown in table 1.

TABLE 1

| Colon release percentage (%) of the tablets from the examples | | | | | | | |
|---|---|---|---|---|---|---|---|
| Example | 1 | 2 | 3 | 4 | 5 | 6 | 7 |
| Colon release percentage of the tablets (%) | 61 | 81 | 76 | 55 | 45 | 58 | 74 |

As can be seen from the results shown in FIG. 1 and table 1, the colon release percentages for all tablets from examples 1-7 could reach above 45%, indicating a remarkable colon targeting effect.

Figure 2:
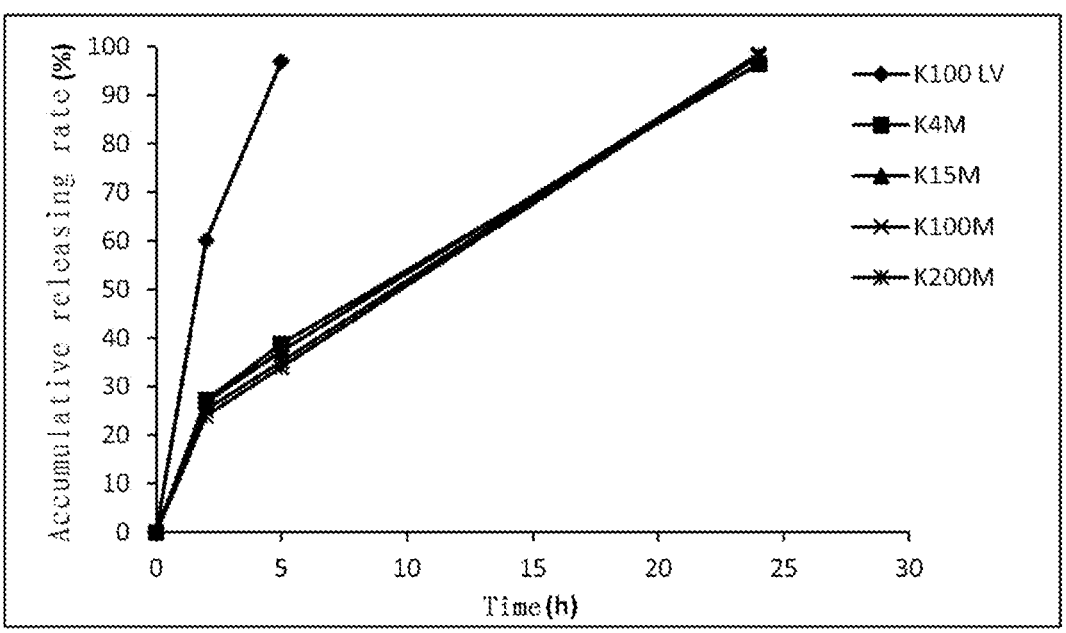
FIG. 2. Graph of dissolution curves of tablets prepared using hydroxypropyl methylcellulose with different viscosities upon subjecting to artificial gastric juice for 2 hours, artificial intestinal juice for 3 hours and artificial colon liquid for 18 hours in sequence.

Experimental Example 2: Dissolution Tests for Tablets Prepared Using Hydroxypropyl Methylcellulose with Different Viscosities According to the methods disclosed in the present invention, tablets were prepared with 90 wt % of hydroxypropyl methylcellulose having five different viscosities (HPMC K100LV with a viscosity of 100 mPa·s, K4M, K15M, K100M, and K200M) and 10 wt % of 5-aminosalicylic acid. Then the dissolution tests were performed for the dissolution results. The results are shown in FIG. 2. As shown from the dissolution results in FIG. 2, the tablet prepared using HPMC with a low viscosity (K100LV) had a release rate of about 100% after subjecting to artificial gastric juice and artificial intestinal juice, and failed to release in colon. On the contrary, the tablet prepared using HPMC with a higher viscosity (K4M, K15M, K100M, or K200M) could at least maintain a release rate of above 60% in colon under the same condition, and had an approximately linear release curve in the artificial intestinal juice, indicating a remarkable colon targeting effect.

Experimental Example 3: Detection Assays for Viable Count

Dissolution was performed for the commercially available tablet Siliankang (a tetralogy of viable *Bifidobacterium* tablet, with 500 mg/tablet, in which *Bifidobacterium infantis*, *Lactobacillus acidophilus* and *Enterococcus faecalis* were not less than $0.5*10^{6}$ cfu/g respectively, *Bacillus cereus* was not less than $0.5*10^{6}$ cfu/g, and the auxiliary materials were starch and milk powder-like material) and tablets prepared in the above examples. And then the viable count was detected.
I. Experiment Method
(1) Culture Medium Preparation
39.7 g of MRS agar powder was added to 600 ml distilled water, and dissolved with heating. The glass culture dishes with the thickness of 2.9 mm were cleaned with tap water, washed with distilled water for three times, and dried in air.
(2) Sterilization
The culture medium and the culture dishes were placed in a sterilization pot, and sterilized at 121° C. and 103.4 kPa for 30 minutes.
(3) The Culture Medium was Placed in a Water Bath Pot with a Temperature of 52° C. Until Use; and the Culture Dishes were Placed at Room Temperature for Cooling Until Use.
(4) Dissolution Conditions
According to the Chinese pharmacopoeia (2015 edition, part four, 0931 dissolution rate and releasing rate determination methods, the first method-rotary basket method, 50 r/min, 37° C.), the commercially available Siliankang tablet was subjected to artificial gastric juice (pH1.2) for 2 h before taken out; the tablets prepared in examples 1-7 were respectively placed into a rotary basket, subjected to artificial gastric juice (pH1.2) for 2 h, artificial intestinal juice (pH6.8) for 3 hours, and then taken out.
II. Culture
Before and after the dissolution processing, the Siliankang tablet and the tablets prepared in examples 1-7 were placed into a glass mortar, ground, and diluted with 50 ml of normal saline. After mixing, 1 ml of the mixture was taken for 10-fold gradient dilution. After dilution, 10 ml dilution for each concentration was taken to spread onto the MRS culture medium. The spread dishes were placed into an anaerobic bag and put in a constant-temperature incubator at 37° C. for an incubation of 48 hours. Finally, the dishes were taken out for colony counting.
III. Results
No colony was found for commercially available Siliankang tablet subjected to artificial gastric juice processing (pH 1.2, 37° C.) for 2 h at $10^{-4}\times$ dilution. Compared with the commercially available Siliankang tablet, the tablets of examples 1-7 showed significantly difference. Each tablet from examples 1-7 subjected to artificial gastric juice (pH 1.2, 37° C.) for 2 h and artificial intestinal juice (pH 6.8, 37° C.) for 3 h still remained a larger viable count. The specific detection results for viable count are shown in table 2. The comparison result indicated that, the probiotic tablet of the present invention enabled the probiotics to successfully resist the stomach and the small intestine environment, so that a certain viable count were remained and delivered to colon for releasing. Further, using the present invention, different strains from different manufacturers could all be protected and delivered to the colon part for releasing.

TABLE 2

Viable count detection results after dissolution of commercially available Siliankang tablet and tablets of examples 1-7

| Sample | Viable count per gram before dissolution (cfu/g) | Dissolution processing | Viable count per gram after dissolution (cfu/g) |
|---|---|---|---|
| commercially available Siliankang tablet | $1.06 \times 10^9$ | pH 1.2, 37° C. for 2 h | 0 |
| Example 1 | $1.48 * 10^{10}$ | pH 1.2, 37° C. for 2 h, followed by pH 6.8, 37° C. for 3 h | $1.1 * 10^8$ |
| Example 2 | $4.4 * 10^{10}$ | | $4.5 * 10^8$ |
| Example 3 | $3.1 * 10^{10}$ | | $2.9 * 10^8$ |
| Example 4 | $6.3 * 10^{10}$ | | $4.0 * 10^8$ |
| Example 5 | $4.5 * 10^9$ | | $3 * 10^7$ |
| Example 6 | $1.6 * 10^{10}$ | | $1.0 * 10^8$ |
| Example 7 | $3.3 * 10^{10}$ | | $3.4 * 10^8$ |

The invention claimed is:

1. A colon-targeted composition of a biological active component, comprising hydroxypropyl methylcellulose, biological active component and auxiliary material, wherein a weight percentage of the hydroxypropyl methylcellulose is 65-90%, a weight percentage of the biological active component is 10-30%, and a weight percentage of the auxiliary material is 0-25%; and wherein a viscosity of the hydroxypropyl methylcellulose is 100,000 mPa·s-200,000 mPa·s and the biological active component is probiotics chosen from the group consisting of *Bifidobacterium lactis, Lactobacillus rhamnosus, Lactobacillus acidophilus, Bifidobacterium longum, Bifidobacterium bifidum* and *Lactobacillus helveticus*.

2. The composition of claim 1, wherein an amount of the probiotics in the composition is 0.001-120 billion cfu/g.

3. The composition of claim 2, wherein the auxiliary material comprises a nutrient substance beneficial to survival stability of the biological active component, a medicinal auxiliary material or a food additive beneficial to colon-targeted delivery of the biological active component, and/or other auxiliary materials for optimizing a property of the composition itself.

4. A colon-targeted formulation of a biological active component, which comprises the composition of claim 2.

5. A colon-targeted formulation of a biological active component, which comprises the composition of claim 1.

6. The colon-targeted formulation of a biological active component of claim 5, wherein a dosage form of the formulation is a tablet.

7. A method for preparing the colon-targeted formulation of a biological active component of claim 6, comprising:
    (1) mixing the hydroxypropyl methylcellulose, the biological active component and the auxiliary material under an operation temperature of <28° C. and a humidity of <40% to form a mixture; and
    (2) dry-pressing the mixture into tablets directly, or dry granulating followed by pressing into tablets.

* * * * *